United States Patent [19]

Temme

[11] 4,216,322
[45] Aug. 5, 1980

[54] PROCESS FOR MAKING TRIETHYLENE DIAMINES

[75] Inventor: George H. Temme, North Haven, Conn.

[73] Assignee: The Upjohn Company, Kalamazoo, Mich.

[21] Appl. No.: 956,109

[22] Filed: Oct. 30, 1978

[51] Int. Cl.² .......................................... C07D 478/08
[52] U.S. Cl. .................................... 544/352; 544/351
[58] Field of Search ................................ 544/351, 352

[56] References Cited

PUBLICATIONS

Shishkin, G. V. Chemical Abstracts vol. 86, 29873y (1977).

*Primary Examiner*—Jose Tovar
*Attorney, Agent, or Firm*—James S. Rose; Denis A. Firth

[57] ABSTRACT

There is disclosed a novel process for the preparation of 1,4-diazabicyclooctane dihydrohalides having the formula

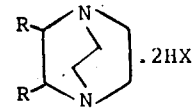

wherein each R is independently selected from the group consisting of hydrogen, lower alkyl, aryl, aralkyl, and cycloalkyl, and X is chlorine or bromine, said process comprising heating at a temperature of at least about 100° C. and in a dipolar aprotic solvent certain novel dihaloalkylene diamines. Neutralization of the dihydrohalides provides the corresponding 1,4-diazabicyclooctane free bases.

Also disclosed are certain novel 1,4-diazabicyclooctane diammonium dihalides formed as intermediates in the above process and a process for their conversion to the 1,4-diazabicyclooctane dihydrohalides and free bases thereof.

The 1,4-diazabicyclo compounds produced in accordance with the invention find particular utility as catalysts in the preparation of polyurethanes from organic polyols and polyisocyanates.

17 Claims, No Drawings

PROCESS FOR MAKING TRIETHYLENE DIAMINES

BACKGROUND OF THE INVENTION

1. Field of the Invention

This invention relates to 1,4-diazabicyclo[2.2.2]octanes and is more particularly concerned with novel processes for their preparation and certain novel 1,4-diazabicyclooctane diammonium dihalide intermediate compounds and novel dihaloalkylene diamine precursors therefor.

2. Description of the Prior Art

The outstanding ability of 1,4-diazabicyclo[2.2.2]octane (also known as triethylenediamine) and related compounds to catalyze the reaction of isocyanates with polyols to form urethanes and, also, the reaction between isocyanates and water to water-blow urethane foams, has long been recognized and utilized by those skilled in the polyurethane foam art; see "DABCO Triethylenediamine, Properties, Reactions and Applications", May 1971, Air Products & Chem. Inc., Wayne, Penna.

The commercial preparation of triethylenediamine, in the main, now requires the use of high temperature-high pressure type reactions which are not energy efficient processes. Typical of such processes is the thermal cracking of diethylenetriamine over a silica-alumina catalyst at 355°–360° C. (U.S. Pat. No. 2,937,176). Another typical process is the treatment of various piperazine stocks, including mixtures of reduction products from ethanolamine (i.e. aminoethylpiperazine, hydroxyethylpiperazine, diethylenetriamine and the like), with a tungsten-aluminum catalyst, or silica-alumina with ammonia at high temperature (e.g. 378° C.); see U.S. Pat. Nos. 3,056,788, 3,120,526, and 3,231,573. Invariably, these methods lead to multi-product mixtures which require complex separation procedures including fractional distillation.

The preparation of triethylenediamine via ring closure of N-($\beta$-cyanoethyl)-N'-($\beta$-chloroethyl)piperazine in a low temperature process has been reported; see U.S.S.R. Pat. No. 519,416 (C.A. 86, 29873y).

It has now been discovered that triethylenediamine and certain derivatives can be prepared in high yields and in a low temperature and energy efficient process based on simple and readily available ethylene diamines thereby eliminating the need for preparing a piperazine starting material. Furthermore, the present process gives rise to but a single product and in a high state of purity thereby obviating the need for complex and expensive separation procedures required by the prior art methods.

After the present invention was made there has been published (Khim. Geterotsikl. Soedin. 1978, (4), page 548–50, published Apr. 5, 1978) a process for the preparation of triethylenediamine by treatment of N,N'-bis($\beta$-cyanoethyl)ethylene diamine with ethylene oxide to give the diol followed by chlorination to yield N,N'-bis($\beta$-chloroethyl)-N,N'-bis($\beta$-cyanoethyl)ethylene diamine which is cyclized and decyanoethylated by boiling in dimethylformamide.

SUMMARY OF THE INVENTION

This invention comprises a process for the preparation of a 1,4-diazabicyclooctane dihydrohalide having the formula

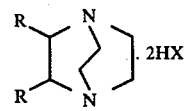

wherein each R is independently selected from the group consisting of hydrogen, lower-alkyl, aryl, aralkyl, and cycloalkyl, and X is selected from the group consisting of chlorine and bromine, said process comprising heating in a dipolar aprotic solvent at a temperature of at least about 100° C., a member selected from the class consisting of a dihalo alkylene diamine having the formula:

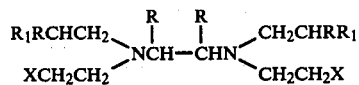

and a 1,4-diazabicyclooctane diammonium dihalide having the formula

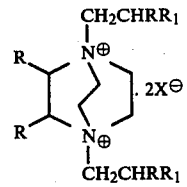

wherein, in each instance, R and X are as defined above and $R_1$ is an electron withdrawing group.

The invention also comprises the compounds (II) and (III).

The invention also comprises the process of preparing the free base 1,4-diazabicyclooctane compounds (IV) corresponding to the dihydrohalides (I) by neutralization of the latter.

The term "lower-alkyl" means alkyl having from 1 to 8 carbon atoms, inclusive, such as methyl, ethyl, propyl, butyl, pentyl, hexyl, heptyl, octyl, and isomeric forms thereof.

The term "aryl" means the radical obtained by removing one nuclear hydrogen atom from an aromatic hydrocarbon having from 6 to 12 carbon atoms, inclusive, such as phenyl, tolyl, naphthyl, biphenylyl, and the like.

The term "aralkyl" means the radical obtained by removing one alkyl hydrogen from an aryl substituted lower-alkane having from 7 to 20 carbon atoms, inclusive. Illustrative of aralkyl are benzyl, p-methylbenzyl, p-ethylbenzyl, $\beta$-phenylethyl, benzhydryl, naphthylmethyl, and the like.

The term "cycloalkyl" means the radical obtained by removing one hydrogen atom from a ring carbon atom of a cycloaliphatic hydrocarbon having from 3 to 8 carbon atoms, inclusive. Illustrative of cycloalkyl are cyclopropyl, cyclobutyl, cyclopentyl, cyclohexyl, methylcyclohexyl, cycloheptyl, cyclooctyl, and the like.

The term "electron withdrawing group" means a group capable of attracting electrons and is inclusive of —CN, —COOR, —CONH$_2$, NO$_2$, SOR, SO$_2$R, and —COR wherein R is defined above.

The free base 1,4-diazabicyclo compounds (IV) prepared in accordance with the present invention are used as intermediates in the preparation of a variety of chemical products. Typically, they form addition compounds with bromine and iodine which addition compounds are used as germicides, bleaching agents, or halogenating agents. Quaternary salts of the diazabicyclo compounds find utility in a number of applications, for example, their mono- and bis-N-phenacyl acid salts possess antibacterial activity.

It is in their role as catalysts that the 1,4-diazabicyclo compounds find particular utility. This includes their catalytic function in the production of both flexible and rigid polyurethane foams and polyisocyanurate foams and as room temperature curatives for polyurethane elastomers. They also play a catalytic role in the dyeing of textiles with reactive dyes.

DETAILED DESCRIPTION OF THE INVENTION

The process in accordance with the present invention can be summarized in the following reaction scheme.

only and is not intended to limit the scope of the present invention in any manner whatsoever.

The course of the conversion and the completion thereof can be observed easily both qualitatively and quantitatively using any convenient analytical means known to those skilled in the art. A particularly preferred method is proton or carbon-13 nuclear magnetic resonance analysis with the proton resonance being used for the quantitative determinations.

Generally speaking, the dihydrohalide (I) will precipitate from the reaction mixture during the course of the reaction. It can be isolated from the reaction mixture by any convenient means known to those skilled in the art, for example, filtration, centrifugation, and the like.

Although not essential, it is convenient to remove overhead distillate during the course of the heating. This ensures optimum conversion of diamine (II) to the desired product (I) and, additionally, represents a purification step. Generally speaking, the combined heating

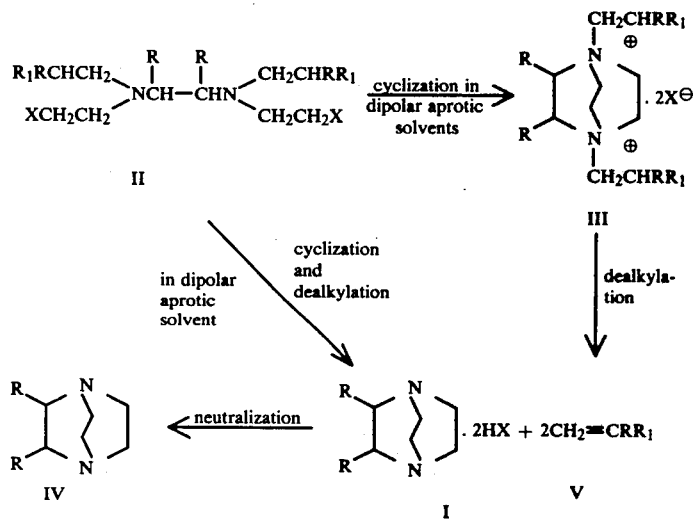

It will be seen that the formation of the desired diazabicyclooctane dihydrohalide (I) can be accomplished in accordance with the invention either by cyclization and dealkylation of the diamine (II) in a single step or by first cyclizing the diamine (II) to the intermediate diammonium halide (III) and then dealkylating the latter. The two step process via the intermediate (III) has the advantage that it generally results in a higher overall yield of the desired compound (I). As will be discussed further below the two step process can be carried out by generating the intermediate (III) in situ and dealkylating the latter without isolation. Alternatively, the intermediate (III) can be prepared and isolated before being subjected to dealkylation.

When the starting diamine (II) is converted in a single step to the desired product (I) this is accomplished readily by heating the diamine (II) in the presence of a dipolar aprotic solvent at a temperature of at least about 100° C. until the formation of the desired product (I) has proceeded to completion. Advantageously, the heating is carried out at a temperature of about 100° C. to about 225° C. and preferably the reaction temperature is within the range of about 125° C. to 200° C. It is presumed that the reaction proceeds through intermediate formation of compound (III) followed by dealkylation of the latter but this is offered by way of explanation and distillation is carried out under atmospheric pressure. Primarily, the overhead distillate consists of solvent and recovered ethylenic compound (V).

The dipolar aprotic solvent employed in the above step can be any one of the solvents falling within this classification well known to those skilled in the art. Illustrative of this class of solvents are the following: dimethylformamide, dimethylacetamide, formamide, acetonitrile, dimethyl sulfoxide, diethyl sulfoxide, tetramethylurea, hexamethylphosphoramide, N-methylpyrrolidone, tetramethylenesulfone, and the like. A preferred solvent in this group is dimethylformamide.

In a preferred embodiment of the present process, the starting compound (II) is cyclized in a first step to the intermediate (III) followed by the dealkylation of compound (III) to compound (I) in a second step. This is accomplished by heating the diamine (II) in the dipolar aprotic solvent at a temperature up to about 95° C., advantageously, from about 70° to about 95° C., preferably from about 75° C. to 85° C. for a period from about 1.0 hour to about 4.0 hours. Then the mixture containing the compound (III) is heated in accordance with the conditions described above for converting (II) directly to (I) by heating at a temperature of at least about 100° C. in the dipolar aprotic solvent. By carrying out the conversion of all the diamine (II) to compound (III) before going on to (I), final yields are maximized.

In a further preferred embodiment the cyclization of compound (II) to compound (III) in the dipolar aprotic solvent is carried out in the presence of an added base to remove the 2 molar proportion of hydrohalic acid which is formed. Although not essential, the removal of the hydrohalic acid in this manner facilitates the conversion to compound (III). The choice of base is not critical and typical bases that can be used are inorganic bases such as calcium carbonate, sodium carbonate, sodium hydroxide, ammonia; organic bases such as triethylamine, tributylamine, and the like. Solvents like dimethylformamide and dimethylacetamide possess enough inherent basicity to remove the hydrohalic acid. A preferred added base is ammonia.

The quantity of base employed is not critical but if optimum conversions are desired then, advantageously, it is used in at least about a 2 molar proportion per mole of (II).

Generally speaking, compound (III) precipitates from the reaction solution even when hot. Accordingly, it can be isolated simply by filtration, if desired, before being converted to the dihydrohalide (I).

Preferably, compound (III) is not isolated but is dealkylated to the dihydrohalide (I) without isolation by heating the reaction mixture obtained directly from the cyclization step in accordance with the conditions described above for converting diamine (II) directly to dihydrohalide (I) by heating at a temperature of at least about 100° C. in the dipolar aprotic solvent.

Alternatively, if the compound (III) has been isolated from the reaction solution it can be dealkylated to the product (I) or the free base thereof (IV) simply by heating compound (III) in an organic solvent, which need not be a dipolar aprotic solvent, in accordance with the temperature conditions described above for converting diamine (II) directly to product (I) or by mixing compound (III) with aqueous base to obtain free base (IV).

The organic solvent employed in the conversion of intermediate (III) to product (I) can be any solvent known to one skilled in the art to be suitable for carrying out a dealkylation reaction. Typical of the classes of solvents useful for such a conversion are aprotic solvents, dipolar aprotic solvents, glycols, and the like.

Illustrative of aprotic solvents are benzene, toluene, xylene, chlorobenzene, dichlorobenzene, methylene chloride, ethylene dichloride, chloroform, carbon tetrachloride, heptane, pyridine, and the like.

Illustrative of dipolar aprotic solvents are those set forth hereinabove.

Illustrative of glycols are ethylene glycol, diethylene glycol, propylene glycol, dipropylene glycol, triethylene glycol; polyethers for example, polyoxyalkylene glycols such as polyoxyethylene glycols prepared by the addition of ethylene oxide to water, ethylene glycol or diethylene glycol, polyoxypropylene glycols prepared by the addition of 1,2-propylene oxide to water, propylene glycol, and the like. The use of glycols to convert compound (III) to product (I) is particularly preferred when the free base product (IV) derived from (I) is to be used ultimately in a glycol solvent as a polyurethane catalyst component.

In a preferred embodiment of the dealkylation of (III) to (I) the diammonium dihalide compound is carried out in the presence of a catalytic amount of a base. Any one of the bases described above can be employed, as well as a precursor of a base such as an organic amine hydrochloride salt.

The amount of base, as noted above, is only a catalytic amount and is advantageously from about 0.1 mole to about 0.3 mole per mole of compound (III).

In still another embodiment in accordance with the present invention the intermediate diammonium salt (III) is dealkylated to (I) and neutralized to (IV) all in one step by mixing (III) with aqueous base. Generally speaking, this step involves simply mixing together (III) with the aqueous basic solution at room temperature for a short period, typically, about 10 minutes to 60 minutes. Elevated temperatures, up to the boiling point (100° C.) of water can be employed but are not generally necessary. The base employed is not critical. Typically, it can be any one of the basic materials set forth above. The quantity of base employed is not critical but if optimum conversions are desired then advantageously, it is used in at least about a 2 molar proportion per mole of (III).

The free base (IV) can be isolated from the solution by any convenient means known to one skilled in the art such as distillation, vacuum concentration followed by trituration with a solvent, and the like.

A particularly preferred method is to carry out the mixing procedure with the aqueous basic solution in the presence of an organic solvent which forms an azeotrope with water. Removal of the precipitated neutralization salts from the water free mixture yields a solution of (IV) which can then be distilled or induced to cause crystallization of the product. Exemplary azeotropic solvents are benzene, toluene, hexane, heptane, and the like.

When (I) is obtained by any of the other embodiments of the process in accordance with the present invention discussed above, its neutralization to the free base (IV) is simply accomplished using any standard method known to one skilled in the art for neutralizing the hydrohalide salt of an organic amine to the free base.

The dihalo alkylene diamine compounds (II) which are employed as starting materials in the process of the invention, may be prepared using any appropriate means known to those skilled in the art. Illustratively, they can be prepared via the reaction of a one molar proportion of the appropriately substituted ethylene dihalide with a two molar proportion of the appropriately substituted secondary amine to provide (II).

In a preferred preparation of the diamines (II) an ethylene diamine (VI) is first alkylated in accordance with standard procedures with at least a one molar excess of an ethylenic compound (V) to yield the disecondary amine (VII) according to the following equation, $$\text{NH}_2\overset{\overset{R}{|}}{\text{CH}}-\overset{\overset{R}{|}}{\text{CH}}\text{NH}_2 + 2\text{CH}_2=\text{CRR}_1 \longrightarrow$$

VI  V

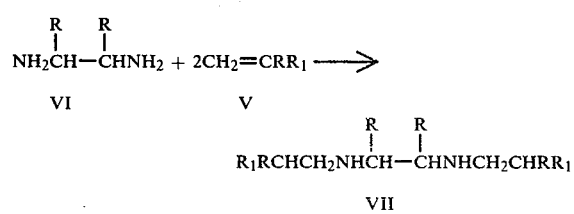

VII wherein, in each instance, R and $R_1$ are as defined above.

The use in the above syntheses of an alkylene diamine analogous to those of formula (VI) but having more than two carbon atoms in the chain connecting the nitrogens, e.g. 1,3-propylene diamine and 1,4-butylene diamine, yields dihalo alkylene diamines analogous to (II) which will not cyclize when subjected to the process of the present invention.

Accordingly, illustrative of the diamines which can be used to prepare the starting diamines (II) in accordance with the present invention are ethylene diamine, 1,2-propylene diamine, 1,2-butylene diamine, 1,2-amylene diamine, 1,2-hexylene diamine, 1,2-heptylene diamine, 1,2-octylene diamine, 2,3-butylene diamine, and the like; 1-phenyl-1,2-ethylene diamine, 1-tolyl-1,2-ethylene diamine, 1-phenyl-1,2-propylene diamine and the like; 1-benzyl-1,2-ethylene diamine, 1($\beta$-phenylethyl)-1,2-ethylene diamine, and the like; and 1-cyclohexyl-1,2-ethylene diamine, 1-cyclohexyl-1,2-propylene diamine, and the like. A preferred group of diamines consists of ethylene diamine, 1,2-propylene diamine, and 2,3-butylene diamine. A particularly preferred diamine is ethylene diamine.

The above-described alkylation of the diamine (VI) is well known to those skilled in the art as a cyanoethylation reaction when the organic electron withdrawing group $R_1$ is a cyano(—CN) group, and, generally speaking, is carried out in accordance with the teaching set forth in Organic Reactions, Vol. V, p. 79, 1949, John Wiley and Sons, Inc., New York.

When the organic electron withdrawing group is other than a —CN group then the reaction is commonly known as a Michael type reaction (see ibid Vol. 10, p. 179 for methods of carrying out this type of reaction).

The term "electron withdrawing group" as used in respect of the group $R_1$ and as defined above is used herein in the sense well known in the art as a group which causes a polarization of the $\alpha,\beta$,-ethylenic compound (V) so as to facilitate the addition of an anionic species at the terminal methylene group; for a discussion of the cyanoethylation and Michael reaction and representative $R_1$ groups see Advanced Organic Chemistry: Reactions, Mechanisms, and Structure, pp. 567–569, 1968 by J. March, McGraw-Hill, New York, N.Y.

Illustrative of the compounds (V) are acrylonitrile, $\alpha$-methylacrylonitrile, $\alpha$-ethylacrylonitrile, $\alpha$-propylacrylonitrile, $\alpha$-butylacrylonitrile, $\alpha$-amylacrylonitrile, $\alpha$-hexylacrylonitrile, $\alpha$-heptylacrylonitrile, $\alpha$-octylacrylonitrile, $\alpha$-phenylacrylonitrile, and the like; acrolein, $\alpha$-methylacrolein, $\alpha$-ethylacrolein, $\alpha$-phenylacrolein, and the like; methylvinyl ketone, ethylvinyl ketone, butylvinyl ketone, hexylvinyl ketone, phenylvinyl ketone, tolylvinyl ketone, and the like; methyl acrylate, ethyl acrylate, phenyl acrylate, $\alpha$-methylmethacrylate, $\alpha$-phenylmethacrylate and the like; acrylamide, $\alpha$-methylacrylamide, $\alpha$-butylacrylamide, and the like; nitroethylene, $\alpha$-methylnitroethylene, $\alpha$-phenylnitroethylene, and the like; methylvinyl sulfone, ethylvinyl sulfone, butylvinyl sulfone, octylvinyl sulfone, phenylvinylsulfone, and the like; methylvinyl sulfoxide, ethylvinyl sulfoxide, butylvinyl sulfoxide, phenylvinyl sulfoxide, p-toluenevinyl sulfoxide, and the like.

A preferred class of compound (V) consists of acrylonitrile, $\alpha$-methylacrylonitrile, $\alpha$-ethylacrylonitrile, $\alpha$-propylacrylonitrile, $\alpha$-butylacrylonitrile, $\alpha$-amylacrylonitrile, $\alpha$-hexylacrylonitrile, $\alpha$-heptylacrylonitrile, $\alpha$-octylacrylonitrile, and $\alpha$-phenylacrylonitrile.

A most preferred compound (V) is acrylonitrile.

The secondary amine (VII) is converted to the corresponding hydroxyethyl derivative (VIII) by replacing each amino hydrogen with the hydroxyethyl group by reacting (VII) with a two molar proportion of ethylene oxide. The use of higher vicinal oxides such as propylene oxide fails to give rise to products which will undergo the process in accordance with the present invention. The ethoxylation is performed using standard methods well known to those skilled in the art.

The novel dihalo alkylene diamines (II) are obtained by the replacement of the hydroxyl groups of (VIII) through chlorination or bromination using standard methods well known to those skilled in the art for converting a hydroxyl group to a chlorine or bromine. The actual halogenation method employed is not critical and any means for carrying out such a conversion may be employed; see Synthetic Organic Chemistry by Wagner and Zook, pp. 89–92, 1953 John Wiley and Sons, Inc., New York, N.Y. for typical halogenation methods. Typical of the chlorinating or brominating agents which can be used are hydrogen bromide, hydrogen chloride, phosphorus tribromide, phosphorus trichloride, thionyl chloride, thionyl bromide phosphorus oxychloride, phosphorus oxybromide, phosgene and the like.

The preferred halogenating agents in accordance with the present invention are the reagents or addition compounds known as Vilsmeier reagents formed from the combination of dimethylformamide and certain inorganic halide reagents such as phosgene, phosphorus oxychloride, thionyl chloride, and the like, simply by mixing the halide reagent and the dimethylformamide together prior to the introduction of (VIII); a most preferred combination is the one formed between dimethylformamide and phosgene. For a discussion of Vilsmeier type reagents and their use in converting hydroxyl groups to halides see, Dimethylformamide Chemical Uses, pp. 81–85, 1967 by R. S. Kittila, Copyright by E. I. DuPont DeNemours & Co., Wilmington, Delaware.

The use of a solvent in the chlorination or bromination is optional. Oftentimes the reactants can serve as their own solvents. In a preferred embodiment an organic solvent is employed. Suitable solvent classes include aprotic solvents and dipolar aprotic solvents, exemplary members of which classes are set forth above. The dipolar aprotic solvents are preferred as a class and the preferred member of this class is dimethylformamide.

Although the chlorinated or brominated product (II) can be isolated from the halogenation mixture using standard separation procedures known to those skilled in the art, in the preferred embodiment in accordance with the present invention the reaction mixture is used directly in the next step without isolation or purification. Accordingly, yields are optimized and the overall procedure simplified. Additionally, dihalo alkylene diamines having the formula (II) tend to possess vesicant properties, therefore, human exposure should be minimized.

When the halogenation step has been carried out in a dipolar aprotic solvent the halogenated product can be left in the same solvent for its conversion to the product (I). In the event that an aprotic solvent was employed in the halogenation then a dipolar aprotic solvent is simply added to the reaction mixture prior to converting (II) to (I) in accordance with the present invention.

The following examples describe the manner and process of making and using the invention and set forth the best mode contemplated by the inventors of carrying out the invention but are not to be construed as limiting.

EXAMPLE 1

A four-neck 250 ml. reaction flask equipped with a mechanical stirrer, thermometer, addition funnel, gas inlet tube, and a reflux-distillation head was charged with 50 ml. of dimethylformamide. Under nitrogen and at a temperature below 10° C., a solution of 17 g. (0.172 mole) of phosgene dissolved in 50 ml. of methylene dichloride was added to the stirred cold dimethylformamide over a period of a half hour.

The flask contents were allowed to return to room temperature (below 25° C.) and 19.66 g. (0.0773 mole) of N,N'-bis($\beta$-hydroxyethyl)-N,N'-bis($\beta$-cyanoethyl)ethylene diamine dissolved in 50 ml. of dimethylformamide was added to the phosgene solution during stirring over a period of a half hour causing the precipitation of a solid complex between the diamine, phosgene, and dimethylformamide. Stirring was continued for an additional half hour at room temperature. Following this, the stirred reaction solution was held at 80°–85° C. for 5 hours. Initially, the original precipitate dissolved but during the heating period another precipitate formed which was N,N'-bis($\beta$-cyanoethyl)triethylenediammonium dichloride.

The reflux-distillation head was adjusted for distillation and, over a half hour period with a pot temperature of 100° to 110° C. and head vapor temperature of 40°–50° (at 760 mm of Hg pressure), there was collected 43.22 g. of distillate which was analyzed by proton nuclear magnetic resonance and shown to consist of 99.8% methylene dichloride, 0.1% acrylonitrile, and 0.1% dimethylformamide. During the initial phase of this heating the solid precipitate dissolved and an obvious crystalline solid reprecipitated. The pot temperature was raised to 140°–150° C. with a head temperature of 70°–135° C. and, over a one hour period, there was collected 40.73 g. of distillate which was analyzed by proton NMR and shown to consist of 59.6% methylene dichloride, 7.7% acrylonitrile and 32.9% dimethylformamide.

The pot residue was cooled to 80° C. and the solid collected by filtration; wt., 12.74 g. C-13 NMR analysis showed it to be 1,4-diazabicyclo[2.2.2]octane dihydrochloride.

The filtrate was diluted with 200 ml. of diethyl ether. A precipitate was filtered and dried to yield 11.48 g. of solid. C-13 NMR analysis showed that the solid consisted of 95% by weight of dimethylamine hydrochloride and 5% 1,4-diazabicyclooctane dihydrochloride.

The total yield of 1,4-diazabicyclooctane dihydrochloride was 93% (based on the diamine II) along with an 86% yield of dimethylamine hydrochloride and a 60% recovery of acrylonitrile.

The 1,4-diazabicyclooctane dihydrochloride was converted quantitatively to the free base 1,4-diazabicyclooctane by neutralization of its aqueous solution with aqueous sodium hydroxide followed by azeotropic distillation of the water with heptane and filtration to remove insoluble salts. Concentration of the heptane solution induced crystallization of the pure base.

EXAMPLE 2

A 250 ml. flask equipped according to Example 1 was charged with 50 ml. of dimethylformamide and, at a temperature of 5°–10° C. and under nitrogen, there was added over a half hour period with stirring a solution of 17.85 g. (0.18 mole) of phosgene dissolved in 50 ml. of ethylene dichloride. Stirring was continued for 1 hour at 5-10° C.

At 20°–25° C. a solution of 20.64 g. (0.081 mole) of N,N'-bis($\beta$-hydroxyethyl)-N,N'-bis($\beta$-cyanoethyl)ethylene diamine dissolved in a mixture of 25 ml. of dimethylformamide and 25 ml. of dichloroethane was added dropwise to the above described phosgene solution over a half hour period and the mixture was stirred for an additional 30 minute period at 20° C. Following this, the stirred reaction mixture was heated for 3.5 hours at 80°–95° C. under nitrogen. Water (0.4 ml.) was added to the hot solution at a temperature of 90° C. to quench the excess phosgene-dimethylformamide complex. Heating of the mixture was continued at 90° C. for a further 4.5 hour period and then it was allowed to cool and stand overnight.

A crystalline precipitate was collected by filtration, washed with methanol and dried to provide 21.72 g. (92% yield) of N,N'-bis($\beta$-cyanoethyl)triethylenediammonium dichloride (analyzed by C-13 NMR). The filtrate and methanol washings combined were concentrated in vacuo to a dark oily solid, wt., 17.89 g. The solid was washed with a 1:1 mixture of isopropanol and methylene chloride to yield 4.22 g. of brown solid which C-13 NMR analysis showed to be dimethylamine hydrochloride containing some impurities. Concentration of the filtrate to 13.67 g. of impure solids and C-13 NMR showed it to be predominantly dimethylamine hydrochloride.

The N,N'-bis($\beta$-cyanoethyl)triethylenediammonium dichloride was recrystallized from hot aqueous ethanol to yield fine needles, m.p. 317°–318° C. (dec.) which contained a half mole of water by hydration, and had the following analysis Calc'd. for $C_{12}H_{20}N_4Cl_2 \cdot \frac{1}{2}H_2O$: C, 48.00%; H, 7.38%; N, 18.66%; Cl, 23.61%. Found: C, 47.82%; H, 7.36%; N, 18.42%; Cl, 23.37%.

Converting N,N'-Bis($\beta$-cyanoethyl)triethylenediammonium Dichloride to Triethylenediamine Dihydrochloride or Free Base Thereof (a) A 334 mg. sample of the pure diammonium chloride was mixed with 2 ml. of diethyleneglycol and heated to 140° C. causing the salt to dissolve. After heating the solution (to or) at 200° C. for 20 min. under atmospheric pressure a distillate was obtained with a boiling range of 80°–120° C., which distillate was shown by C-13 NMR to contain a combination of acrylonitrile and ethylene glycol. The pot residue was analyzed by C-13 NMR and shown to contain triethylenediamine dihydrochloride mixed with acrylonitrile.

(b) A suspension of 5.82 g. (0.02 mole) of the diammonium dichloride in a solution of 0.54 g. (0.0066 mole) of dimethylamine hydrochloride in 25 ml. of dimethylformamide was heated to 150° C. for 2.5 hours. Thereafter a 3.37 g. distillate was collected boiling at 70°–150° C. under atmospheric pressure. Analysis of the distillate by proton nuclear magnetic resonance showed it to consist of a mixture of 1.48 g. of dimethylformamide, 0.3 g. water, and 1.55 g. (0.029 mole) of acrylonitrile (73% recovery).

The reaction residue was cooled and filtered to yield 2.89 g. (78% yield) of triethylenediamine dihydrochloride which was characterized by both proton and C-13 NMR.

(c) A 2.91 g. (0.01 mole) sample of the diammonium dichloride was added to a two phase liquid system consisting of 0.8 g. (0.02 mole) of sodium hydroxide dissolved in 5 ml. of water and 10 ml. of methylene chloride. The two phase system was rapidly stirred together at room temperature for a few minutes. The stirring was stopped and the two layers allowed to separate.

The aqueous phase was washed with 3×10 ml. portions of methylene chloride while the organic phase was washed with 10 ml. of water and this water wash combined with the aqueous phase. The aqueous solution was heated in a Dean-Stark trap with 25 ml. of toluene and the water removed by azeotropic distillation. The dry toluene solution was filtered to yield 7.95 g. of clear solution which contained 0.55 g. (50% yield) of triethylenediamine by C-13 NMR.

EXAMPLE 3

A four-neck 250 ml. reaction flask equipped according to Example 1 was charged with 50 ml. of dimethylformamide and at a temperature of 5°–10° C. and under nitrogen there was added over a half hour period during stirring a solution of 15.19 g. (0.153 mole) of phosgene dissolved in methylene dichloride. The viscous solution was stirred for 45 minutes at 5°–10° C.

A solution of 16.62 g. (0.065 mole) of N,N'-bis(β-hydroxyethyl)-N,N'-bis(β-cyanoethyl)ethylene diamine dissolved in 50 ml. of dimethylformamide was added dropwise to the phosgene solution (obtained as described above) over a 15 minute period at 15°–25° C. Stirring was continued for a further period of 15 minutes and then the temperature was raised to 85° C. causing some methylene dichloride to distil over to a receiver. Heating was continued for 1.25 hours and then 0.9 g. (0.05 mole) of anhydrous ammonia was added via the gas inlet tube. Heating was continued at 85° C. for 30 minutes and another 0.9 g. portion of ammonia added. After another 30 minute heating period another 0.9 g. of ammonia was added representing a total addition of 0.15 mole of ammonia. The reaction mixture was then heated for 2 hours at 85° C. before being left to stand under nitrogen overnight at ambient temperature.

The mixture was heated to 150°–155° C. and overhead distillation of liquid started. At a pot temperature of 90°–120° a fraction boiling at 55° C. and weighing 53.66 g. was obtained. NMR analysis of this fraction identified the constituents as 97.5% methylene dichloride and 2.5% dimethylformamide.

At a pot temperature of 120°–155° C. a fraction boiling at 55°–145° C. and weighing 28.9 g. was collected and analyzed by NMR to consist of 11.0 g. methylene chloride, 12.4 g. dimethylformamide, and 5.5 g. acrylonitrile (80% recovery of the theoretical amount). Heating was stopped when the head vapor temperature reached 145° C.

When the reaction mixture cooled, a crystalline solid, which had formed previously, was isolated by filtration. The collected solid was washed with dimethylformamide followed by 50 ml. of methanol. It was dried to 16.5 g. of light brown powder. Analysis by NMR showed the solid to be a mixture of 5.1 g. (0.095 mole) of ammonium chloride and 11.4 g. (0.061 mole) of triethylenediamine dihydrochloride.

The filtrate was concentrated in vacuo to 4.8 g. of semisolid residue which NMR analysis showed to consist of dimethylformamide and 20–30% dimethylamine hydrochloride plus unidentified by-products.

The 16.5 g. mixture of ammonium chloride and triethylene diamine dihydrochloride obtained above was added in portions to a stirred solution of 10.0 g. (0.25 mole) of sodium hydroxide in 10.3 g. of water. An additional 8.3 g. of water was added to ensure complete solution followed by 75 ml. of heptane and the immiscible mixture heated to reflux using a Dean-Stark trap to remove water by azeotropic distillation. A 23.45 g. aqueous fraction collected from the trap contained 1.69 g. of triethylenediamine by NMR analysis.

The heptane solution was filtered to remove the solid sodium chloride. The solid was washed with 3×25 ml. portions of hot heptane and the washings added to the main heptane solution. The heptane was concentrated by distillation with 87.7 g. of distillate containing 0.12 g. of triethylenediamine. The pot residue was cooled and triethylenediamine crystallized as white prisms. The crystalline product was collected by filtration and dried to yield 3.36 g. of product while the mother liquor contained an additional 0.73 g. of product.

The 5.9 g. total yield of pure triethylenediamine amounted to a 79% overall yield from the starting N,N'-bis(β-hydroxyethyl)-N,N'-bis(β-cyanoethyl)ethylenediamine.

EXAMPLE 4

A 250 ml. flask equipped according to Example 1 was charged with 50 ml. of dimethylformamide, and at a temperature of 5°–10° C. under nitrogen, there was added, over a half hour period with stirring, a solution of 15.22 g. (0.153 mole) of phosgene dissolved in 50 ml. of methylene dichloride.

At 20°–25° C. a solution of 16.5 g. (0.062 mole) of N,N'-bis(β-hydroxyethyl)-N,N'-bis(β-cyanoethyl)-1,2-propylene diamine dissolved in 50 ml. of dimethylformamide was added, over a half hour period, to the above solution of phosgene. Following this, the mixture was heated at 85° C. with constant stirring for 1.5 hours. Then the temperature was raised first to 110° C. and, over a 1.75 hour period, held at about 150° C. Over the whole 3.25 hour heating period overhead distillate was collected. The first 45.82 g. fraction was 99% methylene chloride while the second 14.9 g. fraction contained 45% by weight of acrylonitrile (analyzed by proton NMR).

The reaction mixture was cooled and a solid residue collected by filtration. The crystalline solid so obtained was washed with isopropanol followed by ether and dried to yield 4.9 g. of off-white crystals. C-13 NMR showed the solid to be 2-methyl-1,4-diazabicyclo[2.2.2]octane dihydrochloride; yield 40%. Comparison of this C-13 NMR with that of an authentic sample showed the present sample to be purer. A further 5.90 g. of crystalline solid was collected from the filtrate after standing overnight. This was analyzed by proton NMR and found to be a 9:1 by weight mixture of dimethylamine hydrochloride and 2-methyl-1,4-diazabicyclo[2.2.2]octane dihydrochloride. This additional crop of product raised the total yield to 45% while the yield of dimethylamine hydrochloride was 52.6%.

I claim:

1. A process for the preparation of a 1,4-diazabicyclooctane dihydrohalide having the formula

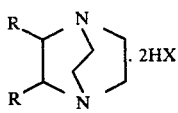 I wherein each R is independently selected from the group consisting of hydrogen, lower-alkyl, aryl, aralkyl, and cycloalkyl, and X is selected from the group consisting of chlorine and bromine, said process comprising heating in a dipolar aprotic solvent at a temperature of at least about 100° C. a member selected from the class consisting of a dihalo alkylene diamine having the formula:

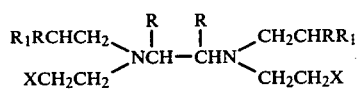 II and a 1,4-diazabicyclooctane diammonium dihalide having the formula:

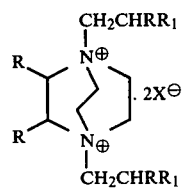 III wherein, in each instance, R and X are as defined above and $R_1$ is an electron withdrawing group.

2. A process according to claim 1 wherein said diazabicyclooctane dihydrohalide is neutralized to form the corresponding 1,4-diazabicyclooctane compound.

3. A process according to claim 1 wherein the 1,4-diazabicyclooctane diammonium dihalide of formula (III) has been obtained by cyclizing the corresponding diamine of formula (II) by heating the latter at a temperature of 70° C. to 95° C. in a dipolar aprotic solvent.

4. A process according to claim 1 wherein $R_1$ in each case is a cyano group.

5. A process according to claim 3 wherein the cyclization is carried out in the presence of an added base.

6. A process according to claim 3 wherein the 1,4-diazabicyclooctane diammonium dihalide is converted without isolation or purification to the corresponding 1,4-diazabicyclooctane dihydrohalide.

7. A process according to claim 3, 4, 5, or 6, wherein said 1,4-diazabicyclooctane dihydrohalide of formula (I) is neutralized to form the corresponding 1,4-diazabicyclooctane free base.

8. A process for the preparation of a 1,4-diazabicyclooctane dihydrochloride having the formula

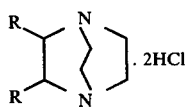

wherein each R is independently selected from the group consisting of hydrogen, lower-alkyl, aryl, aralkyl, and cycloalkyl, said process comprising:
(a) heating a dichloro alkylene diamine having the formula

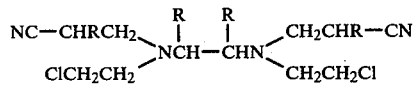

wherein R is defined above, in a dipolar aprotic solvent at a temperature of up to about 95° C. and in the presence of a base to form the corresponding 1,4-diazabicyclooctane diammonium dichloride; and
(b) heating the reaction solution from (a) at a temperature of at least about 100° C. to form said 1,4-diazabicyclooctane dihydrochloride.

9. A process according to claim 8 wherein each of the R groups in said dichloro alkylene diamine are hydrogen whereby there is obtained 1,4-diazabicyclooctane dihydrochloride.

10. A process according to claim 8 or 9 wherein said 1,4-diazabicyclooctane dihydrochloride is neutralized to form the corresponding 1,4-diazabicyclooctane compound.

11. A process comprising the steps:
(a) heating N,N'-bis(β-chloroethyl)-N,N'-bis(β-cyanoethyl)ethylene diamine at a temperature of from about 70° C. to about 95° C. in dimethylformamide and in the presence of ammonia to obtain N,N'-bis(β-cyanoethyl)-1,4-diazabicyclo[2.2.2]octane diammonium dichloride; and
(b) heating the reaction solution from (a) at a temperature of from about 100° C. to about 225° C. to form 1,4-diazabicyclo[2.2.2]octane dihydrochloride.

12. A process according to claim 11 wherein said 1,4-diazabicyclo[2.2.2]octane dihydrochloride is neutralized to form 1,4-diazabicyclo[2.2.2]octane.

13. A process for the preparation of a 1,4-diazabicyclooctane dihydrohalide having the formula

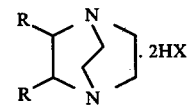

wherein each R is independently selected from the group consisting of hydrogen, lower-alkyl, aryl, aralkyl, and cycloalkyl, and X is selected from the group consisting of chlorine and bromine, said process comprising dealkylating a 1,4-diazabicyclooctane diammonium dihalide having the formula

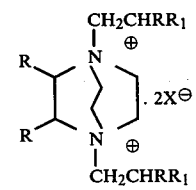

wherein, in each instance R and X are as defined above and $R_1$ is an electron withdrawing group.

14. A process according to claim 13 wherein said dealkylating step comprises heating said diammonium dihalide in an organic solvent with a base to form said 1,4-diazabicyclooctane dihydrohalide.

15. A process according to claim 13 wherein said dealkylating step comprises heating said diammonium dihalide in a glycol solvent to form said 1,4-diazabicyclooctane dihydrohalide.

16. A process according to either of claims 14 or 15 wherein said 1,4-diazabicyclooctane dihydrohalide is neutralized to form the corresponding free base.

17. A process according to claim 13 wherein said dealkylating step comprises treating said diammonium dihalide with aqueous base at ambient temperature to form said 1,4-diazabicyclooctane free base.

* * * * *